United States Patent [19]

Åkerman et al.

[11] Patent Number: 5,994,384
[45] Date of Patent: Nov. 30, 1999

[54] PHARMACEUTICAL COMPOSITIONS OF LEVO-ENANTIOMERS OF MEDETOMIDINE DERIVATIVES AND THEIR USE

[75] Inventors: Karl E. O. Åkerman, Uppsala, Sweden; Christian Jansson, Mariehamn, Finland; Jyrki Kukkonen, Uppsala, Sweden; Juha-Matti Savola, Turku, Finland; Siegfried Wurster, Turku, Finland; Victor Cockcroft, Turku, Finland

[73] Assignee: Orion Corporation, Espoo, Finland

[21] Appl. No.: 09/043,107

[22] PCT Filed: Oct. 23, 1996

[86] PCT No.: PCT/FI96/00560

§ 371 Date: Sep. 16, 1998

§ 102(e) Date: Sep. 16, 1998

[87] PCT Pub. No.: WO97/15302

PCT Pub. Date: May 1, 1997

[30] Foreign Application Priority Data

Oct. 23, 1995 [GB] United Kingdom ............... 9521680

[51] Int. Cl.[6] .................................................. A61K 31/415
[52] U.S. Cl. ........................... 514/397; 514/399; 514/400
[58] Field of Search ................................... 514/397, 349, 514/400

[56] References Cited

U.S. PATENT DOCUMENTS

| | | |
|---|---|---|
| 4,814,343 | 3/1989 | Cossement et al. . |
| 4,923,865 | 5/1990 | Cossement et al. . |
| 5,308,869 | 5/1994 | Keana et al. ............................. 514/637 |
| 5,385,927 | 1/1995 | Michel et al. . |

FOREIGN PATENT DOCUMENTS

| | | |
|---|---|---|
| 72615-B1 | 12/1985 | European Pat. Off. . |
| 300652-A1 | 1/1989 | European Pat. Off. . |
| 341231-B1 | 11/1992 | European Pat. Off. . |
| 269599-B1 | 12/1993 | European Pat. Off. . |
| 626372-A1 | 11/1994 | European Pat. Off. . |
| 91/02505 | 3/1991 | WIPO . |
| 92/21338 | 12/1992 | WIPO . |

OTHER PUBLICATIONS

Savola J.–M., "Cardiovascular Actions of Medetomidine and their Reversal by Atipamezole", Acta vet. Scand., 1989, 85, 39–47.

Coffman J. D. and Cohen R. A., "$\alpha_2$–Adrenergic and 5–HT$_2$ Receptor Hypersensitivity in Raynaud's Phenomenon", J. Vasc. Med. and Biol., 1990, 2(3), 100–106.

Garris D. R., "Age– and diabetes–associated alterations in regional brain norepinephrine concentrations and adrenergic receptor populations in C57BL/KsJ mice", Dev. Brain Res., 1990, 51, 161–166.

Azuma T. et al., "Effect of long–term L–threo–3,4–dihydrophenylserine administration on $\alpha_2$–adrenergic receptors in platelet membranes in neurologic disorders", Acta Neurol. Scand., 1991, 84, 46–50.

Jhanwar–Uniyal M. et al., "Higher $\alpha$–Noradrenergic Receptors in Paraventricular Nucleus of Obese Zucker Rats: Decline After Food Deprivation", Pharmacol. Biochem. & Behav., 1991, 40, 853–859.

Morita T. et al., "Changes of Autonomic Receptors Following Castration and Estrogen Administration in the Male Rabbit Urethral Smooth Muscle", Tohoku J. Exp. Med., 1992, 166, 403–405.

Hong M. et al., "Stereoselective effects of central $\alpha_2$–adrenergic agonist medetomidine on in vivo catechol activity in the rat rostral Ventrolateral medulla (RVLM)", Brain Research, 1992, 592, 163–169.

Tian W.–N. et al., "Determinants of $\alpha_2$–Adrenergic Receptor Activation of G Proteins: Evidence for a Precoupled Receptor/G Protein State", Molecular Pharmacology, 1994, 45, 524–531.

Lockette W. et al., "$\alpha_2$–Adrenergic Receptor Gene Polymorphism and Hypertension in Blacks", Am. J. Hypertens., 1995, 8, 390–394.

Bond R. A. et al., "Physiological effects of inverse agonist in transgenic mice with myocardial overexpression of the $\beta_2$–adrenoceptor", Nature, 1995, 374, 272–276.

Jenkinson D. H. et al., "International Union of Pharmacology Committee on Receptor Nomenclature and Drug Classification. IX. Recommendations on Terms and Symbols in Quantitative Pharmacology", Pharmacol. Rev., 1995, 47(2), 255–266.

Freeman K. et al., "Genetic Polymorphism of the $\alpha_2$–Adrenergic Receptor Is Associated With Increased Platelet Aggregation, Baroreceptor Sensitivity, and Salt Excretion in Normotensive Humans", Am. J. Hypertens., 1995, 8, 863–869.

*Primary Examiner*—Keith D. MacMillan
*Attorney, Agent, or Firm*—Finnegan, Henderson, Farabow, Garrett & Dunner, L.L.P.

[57] ABSTRACT

The levo-isomers of certain imidazole derivatives, particularly medetomidine, have been found to be inverse agonists of adrenergic α-2 receptors and are therefore useful in the prevention or treatment of conditions associated with overexpression or hypersensitization of the adrenergic α-2 receptors, such as obesity, a withdrawal symptom to an adrenergic α-2 receptor agonist, a neurological disorder, multiple system atrophy, diabetes mellitus, benign prostatic hyperplasia, and drug-induced sensitization of adrenergic α-2 receptors. The pharmaceutical composition is preferably transdermal.

9 Claims, 2 Drawing Sheets

PHARMACEUTICAL COMPOSITIONS OF LEVO-ENANTIOMERS OF MEDETOMIDINE DERIVATIVES AND THEIR USE

The invention is related to the use of the levo-enantiomers of certain imidazole derivatives in the prevention or treatment of conditions associated with overexpression or hypersensitization of adrenergic α-2 receptors as well as in the diagnosis of such conditions. The invention is also related to pharmaceutical compositions containing such imidazole derivatives.

The imidazole derivatives used in the invention are either the levo-enantiomers of the compounds of formula I

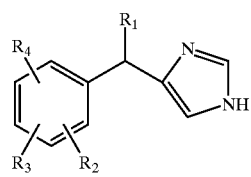

wherein $R_1$ is $C_1$–$C_2$-alkyl and $R_2$ to $R_4$ are each the same or different and are independently hydrogen, $C_1$–$C_2$-alkyl, OH, $OCH_3$, halogen, $C_1$–$C_2$-hydroxyalkyl, carboxy, cyano, CHO, $COOCH_3$, $COOCH_2CH_3$, $CONH_2$, C=$NHNH_2$, C=$NHNHCH(C_6H_6)CH_3$ or physiologically acceptable esters or salts thereof with the proviso that more than one of the substituents $R_2$ to $R_4$ are not at the same time C=$NHNHCH(C_6H_6)CH_3$.

Preferred compounds are those in which $R_1$ is methyl and $R_2$, $R_3$ and $R_4$ are each independently hydrogen, $C_1$–$C_2$-alkyl, hydroxy, $C_1$–$C_2$-hydroxyalkyl or $CONH_2$. The levo-enantiomer of medetomidine is particularly preferred.

The preparation of the imidazole derivatives of formula I in general has been described, for example, in EP 72 615 B1, EP 269599 B1, EP 341231 B1 and in EP 626372 A1. The corresponding levo-enantiomers may be prepared, e.g. using optically active acids as described in EP 300652 B1.

Although some of the derivatives of formula I are known from the literature (mostly as a component of the corresponding racemic mixture), it is believed that their use as a medicament or as a diagnostic agent in a form such that the presence of the corresponding dextro enantiomer is limited to insignificant amounts i.e. as an impurity has never been disclosed.

It has now been surprisingly observed that the levo-enantiomers of the imidazole derivative of the formula I are true inverse agonists of adrenergic α-2 receptors. This means that the compounds of the invention may be used in the prevention or treatment of conditions associated with overexpression or hypersensitization of adrenergic α-2 receptors.

With the development of sensitive test systems detection of inverse agonism has become possible, making it necessary to reclassify many pharmacological agents (Bond, R. A. et al., 1995, Nature, 374, 272). An inverse agonist appears to destabilize receptor-G protein coupling or to bind selectively to the inactivated form of the receptor (or both). In systems where there is considerable formation of the activated receptor system (constitutively activated receptors i.e. receptors which are active in the absense of an agonist) compounds with inverse agonist properties will alter the equilibrium between active and inactive receptors, increasing the number of receptors in inactivated form. This, in turn, results in the reduction of the number of receptors which are actively participating in the signal transduction (inverse agonism, which can also be called as negative antagonism). In bried, an inverse agonist is a drug that by binding to receptors reduces their fraction in active conformation (Jenkins, D. H., et al., 1995, Pharmacol. Rev., 47, 255).

Inverse agonists may be particularly important in disease states and in pathogenesis which result from mutations in constitutively activated receptors. Inverse agonists, therefore, represent an important and specific therapeutic approach for such disease states.

Previously inverse agonists have been found in the family of antagonists (Bond et al., 1995 and Wang-Ni T. et al., 1994, Molecular Pharmacology, 45, 524). However, antagonist type of inverse agonists besides negating constitutive receptor activity also eliminate endogenous agonist tone in all tissues which is not desired in targeted drug therapy.

A true inverse agonis, like a compound of the invention reduces receptor activation state and, therefore, represent the key to the above described targeted agents to diagnose, prevent or treat disease states related to constitutively active receptors.

Inverse agonists of adrenergic α-2 receptors can be used in the treatment of disease states associated with increased receptor number or sensitivity either alone or together with adrenergic α-2 receptor agonists or adrenergic α-2 receptor antagonists as conventionally defined. True inverse agonists of adrenergic α-2 receptors can be used to treat Raynaud phenomenon (Coffman, J. D. and Cohen, R. A., J. Vasc. Med., Biol., 3, 100), hypertension, stroke and other pathological and clinical disorders related to genetic polymorphism of the α-2 receptors (Freeman, K., et al., 1995, Am. J. Hypertens., 8, 863; Lockette, W., 1995, Am. J. Physiol., 8, 390), obesity (Jhanwaruniyal, M. et al., 1991, Pharmacol. Biochem. Behav., 40, 853), withdrawal symptoms to clonidine and other adrenergic α-2 receptor agonists, neurological disorders featured by sympathetic nervous system dysfunction (such as orthostatic hypotension in Parkinson's disease) and multiple system atrophy (Azuma, T. et al., 1991, Acta Neurol. Scand., 84, 46), diabetes mellitus (Garris, D. R., 1990, Dev. Brain Res., 51, 161), benign prosthatic hyperplasia and other disease states where sex and other steroids have caused upregulation of adrenergic α-2 receptor agonists (Morita, H. et al. 1992, Tohoku. J. Exp. Med., 166, 403) and other drug-induced sensitization of adrenergic α-2 receptors, such as treatment of depression with mianserin or shcizophrenia with olenzapine or clozapine, treatment of rheumathoid arthritis or asthma with dexamethasone or other steroids, or treatment of hypertension with reserpine or other sympatholytics.

It is important for an effective use of the compounds of the invention that the amount of the corresponding dextro enantiomer (i.e. the agonist) is not so high that it interferes with or even neutralises the action of the inverse agonist. The maximum amount of the dextro enantiomer depends, of course, on the properties of the two enantiomers in each case and it is believed that the amount can be calculated without undue experimentation by a person having average skill in the art. For example, in case of levomedetomidine the maximum amount of dexmedetomidine is about 0.3 weight percent of the total amount of both enantiomers, preferably 0.1 percent by weight.

It is another object of the invention to provide a pharmaceutical composition which contains as an active ingredient a derivative of formula I, wherein the amount of the dextro enantiomer of the said active ingredient is preferably less than 0.3 weight percent of the total amount of both enantiomers. Especially preferable are formulations wherein the amount of the dextro enantiomer is less than 0.1 percent by weight of the total amount of the two enantiomers. It is to be noted that the composition may also be totally void of the dextro enantiomer. For practical and economical reasons, however, it is often very difficult to remove the other enantiomer in its entirety.

The compounds of the invention may be formulated alone or together with another active ingredient and a pharmaceutically acceptable diluent or carrier to different pharmaceutical unit dosage forms i.e. tablets, capsules, solutions, ointments, emulsions, lotions, gels, creams, patches and powders etc. using conventional techniques. Especially preferable are formulations which may be administered transdermally.

The pharmaceutical ingredients employed are selected with the planned manner of administration in mind. Thus, solid ingredients may include e.g. sugars and sugar alcohols such as lactose, glucose, sucrose, dextrose, mannitol and sorbitol, starch, cellulose and its derivatives, alginates, synthetic polymers such as polyvinylpyrrolidone, talc, stearic acid salts and its derivatives, while liquid ingredients typically include water, polyhydric alcohols such as glycerol, propylene glycol and polyethylene glycols, mineral oil and vegetable oils. Ingredients for semi-solid products may include above mentioned ingredients and further lanolin, paraffin wax, polyethylene waxes, plant waxes, beeswax, xanthan gum, long-chained alcohols and fatty-acids, carboxyvinyl polymers, sodium lauryl sulphate, sorbitan esters, polyoxyethylene sorbitan eslers as well as polyoxyethylene glycol esters.

The amount of the active ingredient varies from 0.001 to 75 weight %, prefeferably 0.01 to 10 weight % depending on the type of the dosage form.

Transdermal patches for the compounds of the invention may be prepared, for example, as described in PCT Patent application WO 91/02505 for dexmedetomidine (free base) and in PCT Patent application WO 92/21338 for medetomidine (salt).

The appropriate dosage for the compounds of the invention depends on several factors such as the compound to be administrated, the species, age and the sex of the subject to be treated, the condition to be treated and on the method of administration. Accordingly, the dosage for parenteral administration is typically from 0.5 $\mu$g/kg to 10 mg/kg per day and that for oral administration is from 5 $\mu$g/kg to 100 mg/kg for an adult male human.

Preparation of Levomedetomidine

Levomedetomidine, the (−)-enantiomer of medetomidine can be resolved in the same way as dexmedetomidine (EP 300 652 B1), but instead of using L-(+)-tartaric acid as a resolving agent, D-(−)-tartaric acid can be used to give the D-(−)-tartaric acid adduct of the (−)-enantiomer. The purity of the tartrate of the I-enantiomer can be checked e.g. by HPLC so that the recrystallizations are repeated until the content of dexmedetomidine is below 0.3 weight percent of the total amount of both enantiomers. The free base and the corresponding hydrochloride can be made using conventional techniques. Levomedetomidine, base: mp 149–151° C., $[\alpha]D^{20}$ −75.2 (c, 1 g/100 ml MeOH) Levomedetomidine, hydrochloride salt: mp 156–158° C., $[\alpha]D^{20}$ −53.5 (c, 1 g/100 ml H$_2$O).

HEL (human erythroleukemia) cells were derived from the blood of a patient with Hodgkin's disease and erythroleukemia (Martin, P. and Papayannopoulou, 1982, Science 216, 1233). This cell line has been used as a model system for studying adrenergic $\alpha$-2 receptors and their coupling to inhibition of adenylyl cyclase (McKernan et al., 1987, Mol. Pharmacol. 32, 258) and mobilization of intracellular Ca$^{2+}$ (Michel, M. et al, 1989, J. Biol. Chem. 264, 4986 and Musgrave, I. F. and Seifert, R., 1995, Biochem. Pharmacol., 49, 187). Taking the data together it has been demonstrated that HEL cells have a adrenergic $\alpha$-2 receptor suptype that activate pertussis toxin-sensitive G-protein resulting in Ca$^{2+}$ mobilization, via non-selective cation channels, and inhibition of adenylyl cyclase. This system was used to screen different adrenergic $\alpha$-2 receptor agonists for functional purposes.

Measurement of Intracellular Ca$^{2+}$

The intracellular free Ca$^{2+}$ concentrations in HEL cells was determined using fura-2 (Grynkiewicz, G. et al, J. biol. Chem. 260, 3440) as described by Kukkonen et al. (1992, J. Pharmacol. Exp. Ther. 263, 1487). The cells were loaded with fura-2/AM (Molecular probes, Junction City, USA). The cell suspension was then placed in a quartzmicrocuvette and fluorescence measurements were performed with a Hitachi F-2000 fluorescence spectrofotometer at the wavelengths of 340 nm (emission) and 505 nm (excitation). The dye responses were calibrated by sequential addition of digitonin and EGTA at the end of the experiment to obtain maximal and minimal fluorescence values, respectively.

Figure 1:
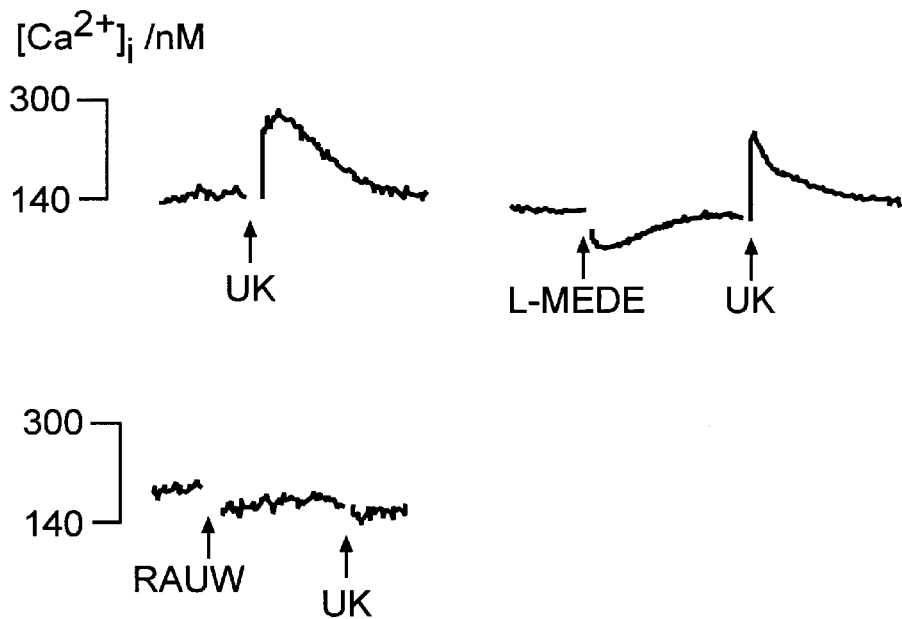
FIG. 1 Measurement of intracellular Ca$^{2+}$ concentrations; UK: 10 $\mu$M UK 14,304 (primonidine), I-mede:10 $\mu$M I-medetomidine,
rauw: 1 $\mu$M rauwolscine.
Figure 3:
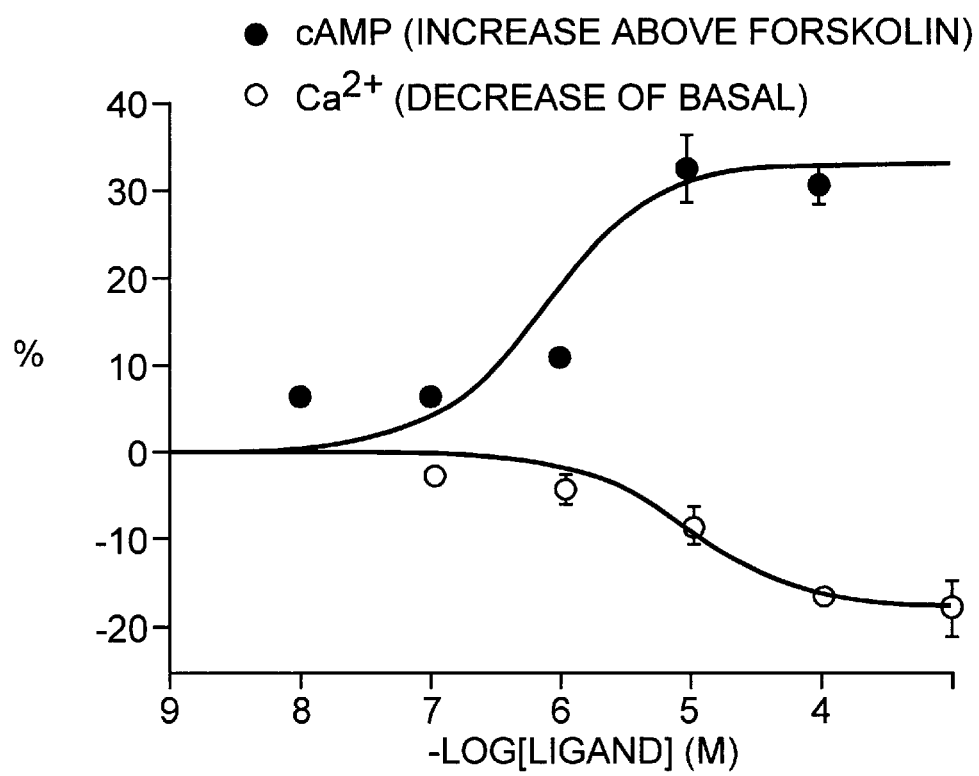
FIG. 3 Dose-response curvers for the effects of I-medetomidine on Ca$^{2+}$ mobilization and cAMP production.
Figure 2:
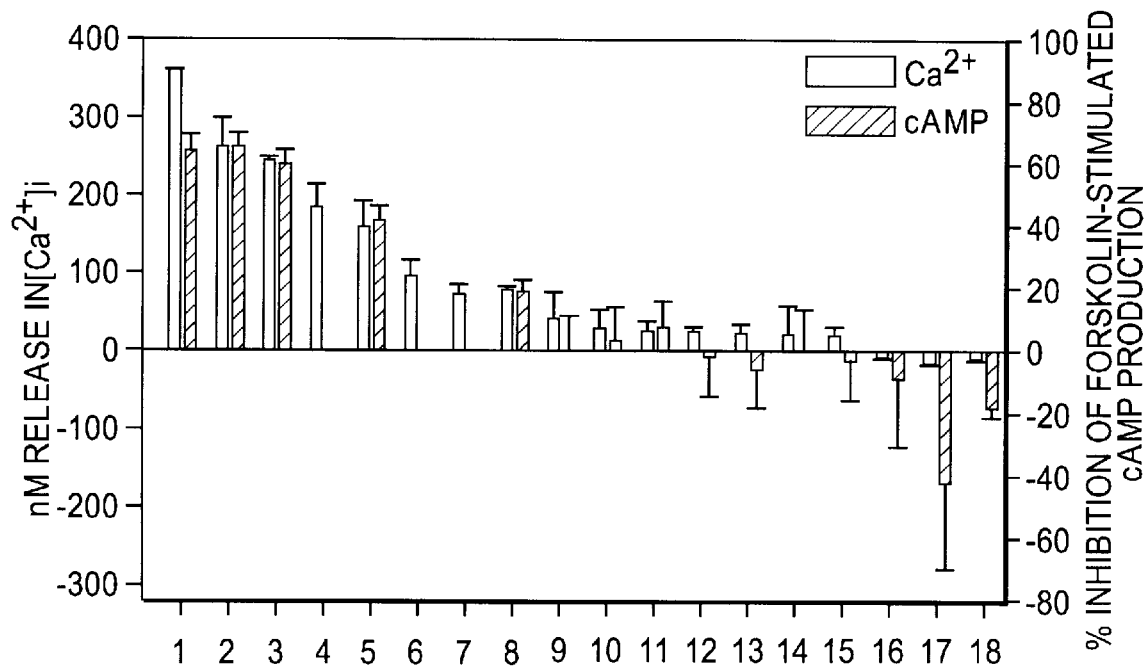
FIG. 2 Maximal responses, of different adrenergic $\alpha$-2 receptor agonists (10 $\mu$M) on Ca$^{2+}$ molibization and cAMP production.

Addition of different adrenergic $\alpha$-2 receptor agonists resulted in a dose-dependent increase in the intracellular concentration of Ca$^{2+}$. Addition of 10 $\mu$M I-medetomidine resulted instead in a decrease (−17±2 nM) of the concentration of Ca$^{2+}$ level (FIG. 1 and FIG. 2). This response was dose-dependent, EC$_{50}$=761±502 nM (FIG. 3). A prior administration of levo-medetomidine did not antagonise receptor activation to UK, an agonist of $\alpha$-2 receptors whereas that of rauwolscine did (FIG. 1).

Measurement of Intracellular cAMP

The intracellular concentration of cAMP was measured by prelabelling the cells with [$^3$H]adenine (Amersham, UK) as described by Jansson et al (1985, Eur. J. Pharmacol. 2613, 165). Separation of [$^3$H]ATP and [$^3$H]cAMP was achieved by the method of Salomon et al. (1974, Anal. Biochem. 58, 541). Conversion of cell-associated [$^3$H]ATP to [$^3$H]cAMP was expressed as a percentage of the total radioactivity and normalized to the percentage recovery of [$^{14}$C]cAMP tracer.

Addition of forskolin resulted in a 10 fold increase in the production of cAMP. Addition of different adrenergic $\alpha$-2 receptor agonists resulted in a dose-dependent inhibition of forskolin stimulated cAMP production. Addition of 10 $\mu$M I-medetomidine resulted in a further stimulation of forskolin stimulated cAMP production (42±27%) (FIG. 2). This response was dose-dependent, EC$_{50}$=150±105 nM (FIG. 3).

These results show that I-medetomidine has opposite effects compared to adrenergic $\alpha$-2 receptor agonists in the concept of coupling to the signal molecules Ca$^{2+}$ and cAMP and that it is able to reduce the constitutive activity of $\alpha$-2 receptors in HEL cells.

EXAMPLE 1

A typical transdermal formulation (a cream) of levomedetomidine may be prepepared as follows:

0.05–0.5 w %, preferably 0.1–0.3 w % of the active ingredient as levomedetomidine hydrochloride or base, 1–40 w %, preferably 5–20 w % of emollient, such as vegetable oils, glycerin and propylene glycol, 1–35 w %, preferably 2–20 w % of emulsifier such as sodium lauryl sulphate, sodium cetostearyl sulphate, polyethylene glycols and glycol stearate, polyethylene glycol glyceryl oleate or laurate or linoleate 0–30 w %, preferably 2–20 w % of consistency agent, such as cetearyl alcohol, glyceryl stearates 0–10 w %, preferably 0.1–2 w % of preservative, such as methyl-, ethyl, propyl- and butylparahydroxybenzoate and phenoxyethanol 30–90 w %, preferably 60–85 w % of purified water In a suitable vessel ernulsifiers, emollients and consistency agents are melted. Preservatives are dissolved by boiling in purified water (a part) in another vessel. Both liquids are adjusted into same temperature (about 80° C.) and combined in a manufacturing vessel. The mixture is homogenized and allowed to cool to 35° C. by continuous mixing under a vacuum. The active ingredient is dissolved in purified water (the rest) and added into the manufacturing vessel. The cream is homogenized and then cooled to room temperature by continuous mixing under a vacuum.

We claim:

1. A method for the prevention or treatment of a condition associated with overexpression or hypersensitization of adrenergic α-2 receptors, comprising administering to a subject in need of such prevention or treatment an effective amount of an imidazole derivative, wherein said imidazole derivative is a levo-enantiomer of a compound of formula I

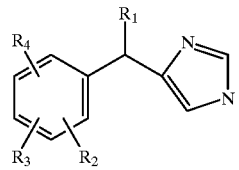

I wherein $R_1$ is $C_1$–$C_2$-alkyl, and wherein $R_2$, $R_3$, and $R_4$ are the same or different and are hydrogen, $C_1$–$C_2$-alkyl, OH, $OCH_3$, halogen, $C_1$–$C_2$-hydroxyalkyl, carboxy, cyano, CHO, $COOCH_3$, $COOCH_2CH_3$, $CONH_2$, C=$NHNH_2$, C=$NHNHCH(C_6H_6)CH_3$ or a physiologically acceptable ester or salt thereof, wherein more than one of $R_2$, $R_3$, and $R_4$ are not at the same time C=$NHNHCH(C_6H_6)CH_3$.

2. The method according to claim 1, wherein $R_1$ is methyl, and wherein $R_2$, $R_3$, and $R_4$ are the same or different and are hydrogen, $C_1$–$C_2$-alkyl, OH, $C_1$–$C_2$-hydroxyalkyl or $CONH_2$.

3. The method according to claim 1, wherein the imidazole derivative is levomedetomidine.

4. The method according to any one of claims 1 to 3, wherein the condition to be prevented or treated is Raynaud phenomenon, hypertension, stroke, obesity, a withdrawal symptom to an adrenergic α-2 receptor agonist, a neurological disorder, multiple system atrophy, diabetes mellitus, benign prosthatic hyperplasia or a drug-induced sensitization of adrenergic α-2 receptors.

5. The method according to claim 4, wherein the neurological disorder to be prevented or treated is orthostatic hypotension.

6. The method according to claim 4, wherein the drug-induced sensitization of adrenergic α-2 receptors is induced by mianserin, olenzapine, clozapine or a steroid.

7. The method according to claim 1, wherein the levo-enantiomer of the compound of formula I is used in combination with an adrenergic α-2 receptor agonist or an adrenergic α-2 receptor antagonist.

8. A method for diagnosing conditions associated with overexpression or hypersensitization of adrenergic α-2 receptors, comprising administering to a subject in need of such diagnosing an effective amount of an imidazole derivative according to any one of claims 1 to 3.

9. A method for diagnosing conditions associated with overexpression or hypersensitization of adrenergic α-2 receptors, comprising administering to a subject in need of such diagnosing an effective amount of an inverse agonist of adrenergic α-2 receptors.

* * * * *